United States Patent [19]

Cochrum

[11] Patent Number: 5,614,204

[45] Date of Patent: *Mar. 25, 1997

[54] ANGIOGRAPHIC VASCULAR OCCLUSION AGENTS AND A METHOD FOR HEMOSTATIC OCCLUSION

[75] Inventor: Kent C. Cochrum, Davis, Calif.

[73] Assignee: The Regents of the University of California, Oakland, Calif.

[*] Notice: The term of this patent shall not extend beyond the expiration date of Pat. No. 5,570,102.

[21] Appl. No.: 377,928

[22] Filed: Jan. 23, 1995

[51] Int. Cl.$^6$ .............................. A61F 2/02; A61K 31/74; A61L 25/00

[52] U.S. Cl. ...................... 424/423; 424/78.08; 424/445; 602/43; 602/52; 128/DIG. 22

[58] Field of Search ..................... 514/772.2; 424/78.08, 424/423, 445; 602/43, 52; 128/DIG. 22

[56] References Cited

U.S. PATENT DOCUMENTS

| | | | |
|---|---|---|---|
| 4,744,933 | 5/1988 | Rha et al. | 264/4.3 |
| 4,749,620 | 6/1988 | Rha et al. | 428/402.2 |
| 5,084,350 | 1/1992 | Chang et al. | 435/240.22 |
| 5,510,102 | 4/1996 | Cochrum | 424/78.08 |

OTHER PUBLICATIONS

Aebischer et al., *Chemical Abstracts*, vol. 114, #103328.
Sugyama, *Chemical Abstracts*, vol. 122, #128074.
Watanabe et al., *Chemical Abstracts*, vol. 115, #263322.
Saito et al., *Chemical Abstracts*, vol. 114, #20502.

*Primary Examiner*—Carlos Azpuru
*Attorney, Agent, or Firm*—Hana Verny

[57] ABSTRACT

Angiographic vascular occlusion agents comprising a biopolymer alone or in combination with platelet-rich plasma. A liquid biopolymer gels in situ in contact with divalent cations. Biopolymer agent achieves permanent occlusion, biopolymer combined with the platelet-rich plasma achieves temporary or semi-permanent occlusion. The plasma is obtained from the patient's own blood to avoid undesirable immunogenic reactions. The occlusion agents have strong occlusive properties when injected into a bleeding vessel.

29 Claims, 3 Drawing Sheets

ANGIOGRAPHIC VASCULAR OCCLUSION AGENTS AND A METHOD FOR HEMOSTATIC OCCLUSION

BACKGROUND OF THE INVENTION

Field of Invention

This invention concerns a novel type of angiographic vascular occlusion agents. In particular, this invention concerns the angiographic vascular occlusion agents prepared from a biocompatible polymer alone to achieve a permanent occlusion or in combination with a platelet-rich plasma concentrate to achieve a semi permanent or temporary occlusion. In the preferred form, the plasma concentrate is obtained from the patient's own blood to avoid undesirable immunogenic reactions. The polymer agents gel and assert hemostatic properties when injected into a bleeding vessel or tissue where they form or facilitate the rapid formation of a permanent polymer clot. In case of the polymer plasma rich containing agents, following the formation of polymer clot, the plasma proteins and platelets quickly trigger the normal clotting mechanism in order to reinforce the clot.

BACKGROUND ART AND RELATED ART DISCLOSURES

In the past ten years, selective vascular embolization and other mechanical occlusive techniques have become increasingly popular methods of treating acute hemorrhage vascular tumors, arterio-venous malformations and organ ablation. Using these occlusive techniques or embolic therapy, a treatment of acute hemorrhage can be accomplished safely and rapidly. Embolic therapy is preferred over other methods of treatment because it avoids both the systemic effects of vasopressin and the need for long-term catheterization of the femoral artery which accompany with other treatment procedures.

Embolic therapy is useful and became a method of choice in many different areas. The embolization is useful to stop mucosal or internal bleeding, and, for example, it became the method of choice for treating esophageal arterial and gastric mucosal bleeding, for treatment of bleeding duodenal ulcers and bleeding from branches of the left gastric artery. *A.J.R.* 133:643 (1979).

Embolization is also useful for stopping bleeding from organs or tissues which are not readily accessible or do not respond to normal hemostatic methods. For example, the vascular beds of the kidneys, liver, and pelvis do not respond well to vasopressin and, therefore, hemorrhage from these organs is best treated by selective embolization. Renal hemorrhage secondary to trauma or tumor also can be successfully treated with selective embolization. (*Radiology*, 130:1 (1979) and *Radiology*, 109:65 (1973)).

Additionally, embolization of thoracic intercostal arteries has been used to control hemorrhage in breast carcinoma and trauma (*Surgery*, 81:409 (1977)); hemoptysis in cystic fibrosis, tuberculosis and bronchiectasis has been controlled by embolization (*Radiology* 122:33 (1977)); epistaxis and hemorrhage resulting from head and neck tumors has been treated by embolization of the branches of the external carotid arteries (*Radiology* 133:639 (1979)), and esophageal varices had been successfully obliterated by embolic therapy (*Radiology* 122:59 (1977)).

Preoperative embolization of vascular tumors, such as renal tumors, meningiomas and juvenile angiofibromas, is able to reduce blood loss during surgery (*J. Neurosurg.* 125:275 (1975)). An additional benefit of embolization to preventing blood loss during surgical removal of renal tumors may be, for example, a diminished spread and seeding of metastases. Selective embolization also is applicable in areas such as arteriovenous malformations and fistula in solid organs such as liver and kidney.

Previously, various methods of vascular occlusion have been used. Muscle or subcutaneous tissue fragments were one of the earliest embolic materials used. However, because use of this material requires an additional incision, embolization using these tissues has been largely abandoned. Blood clots also were used as an embolic material since they can be obtained quite easily. Autologous blood clot was the first embolic material used by a large group of angiographers. In this technique, twenty to 50 cc of the patient's blood is removed via the intraarterial or venous catheter. Blood is then mixed with topical thrombin, a strand of clotted blood is placed into a syringe filled with contrast material and injected. The addition of epsilon-aminocaproic acid to the blood provides a more stable clot and delays lysis.

One of the most useful embolization techniques is a transcatheter hemostatic technique, such as one described in *Radiology* 113:277–285, (1974).

Recently, materials such as Gelfoam, Ivalon, Oxycel and other particulate materials were introduced as useful occlusion materials.

Surgical Gelfoam, a solid slowly absorbed gelatin, probably is the most widely used embolic agent today. Gelfoam is supplied in sterile pads. Individual pieces are cut from these sterile pads of surgical Gelfoam and several small emboli are placed in a syringe and slowly injected through a catheter. As the occlusion progresses more proximally, increasingly larger emboli are used. Gelfoam does not provide permanent occlusion. Within several days most vessels recanalize. A primary disadvantage of Gelfoam is that it has to be injected in solid foam form. When the larger emboli are needed, the foam often blocks the catheter and a guidewire must be used to push and fragment the foam material. This may require strong force which may be dangerous since the generated force can cause the catheter tip to recoil and cause embolic reflux or the tip may cause vessel wall injury. Also, if the cut pieces of foam are too small, they may not occlude the vessel but enter the circulation and cause embolic infarction. If, on the other hand, the foam pieces are too large, they may occlude bigger vessels in other places than where the occlusion is needed.

Ivalon, a solid polyvinyl alcohol foam, is used as a permanent occluding agent. The material must be thoroughly washed with saline and then cut into small pieces for embolization. Small pieces of Ivalon can be injected through catheters, however, its injection through polyethylene catheters can be difficult because of its high friction coefficient. As the most catheters are made of polyethylene, the practical use of Ivalon is severely limited.

Other embolic inducers, such as stainless steel coils, are used to embolize vessels by attaching thrombogenic fibers to a coiled piece of guidewire and passing it through an angiographic catheter to permanently occlude an arterial lumen.

Other methods of obstructing blood flow in a vessel are by balloon occlusion or by creating an intentional intimal dissection and positioning it to completely obstruct blood flow. However, these techniques require surgical invasion of the patient body.

Selective vascular occlusion therapy is a very effective means for achieving hemostasis as it can be performed quickly and safely. However, the primary disadvantage of the previously known vascular occlusion techniques is that the effects of standard selective embolization are uncontrollable, irretrievable or irreversible. These properties are in many cases undesirable. For example, when Gelfoam or Ivalon are used, both these materials must be cut into small pieces of solid material, then these pieces must be injected via a catheter which may get clogged. Throughout this process they must be handled under sterile conditions. When these pieces are too small they fail to achieve occlusion or the occlusion is incomplete so that bleeding continues, or when they are too large they can occlude the vessel above the site of bleeding. Moreover, there is always a risk of introducing the infection. Therefore, it would be advantageous to provide a new and different type of permanent or temporary angiographic vascular occlusion agent that should be more controllable and easier to use. Such vascular occlusion agent should provide the rapid occlusion hemostasis. Such occlusion should be permanent, temporary or semi-permanent and reversible, when necessary, by using a polymer or a polymer and platelet rich plasma containing agent. This would be a major safety advantage over the irretrievable and irreversible effects of Gelfoam, Ivalon sponge, and stainless steel coils. In case of the permanent occlusion, the new type of occlusion agent should be able to form the spheres or occlusive particles in situ of the exact sizes needed to achieve permanent, semi-permanent or temporary occlusion without risking or causing circulating emboli infarction caused by too small particles.

It is, therefore, a primary object of this invention to provide a novel type of permanent, semi-permanent, temporary and reversible angiographic vascular occlusion agents that would provide improved vascular occlusion over the current methods available. In the most preferred forms, these agents are prepared from various biocompatible polymers alone or in combination with a platelet-rich plasma, obtained preferably from the patient's own blood.

The use of autologous platelet-rich plasma and biocompatible polymer containing agents in an angiographic vascular occlusion method has not been previously reported or disclosed.

All patents, patent applications and references cited within are hereby incorporated by reference.

SUMMARY

One aspect of the invention is an angiographic vascular occlusion agent comprising a biocompatible polymer.

Another aspect of the invention is an angiographic vascular occlusion agent comprising a biocompatible polymer selected from the group consisting of an alginate, chitosan and poly-L-amino acid.

Yet another aspect of the invention is an angiographic vascular occlusion agent selected from the group consisting of sodium alginate, potassium alginate, strontium alginate, barium alginate, magnesium alginate or any other alginate or a mixture thereof.

Another aspect of the invention is an angiographic vascular occlusion agent comprising sodium alginate.

Still another aspect of the invention is an angiographic vascular occlusion agent comprising a chitosan.

Still yet another aspect of the invention is an angiographic vascular occlusion agent selected from the group consisting of chitin, cationic chitosan, anionic chitosan or chitosan polyamine.

Still another aspect of the invention is an angiographic vascular occlusion agent selected from the group consisting of poly-L-lysine, poly-L-arginine, poly-L-glutamic acid, poly-L-histidine, poly-α-D-glutamic acid or a mixture thereof.

Still another aspect of the invention is an angiographic vascular occlusion agent comprising poly-L-lysine.

Still yet another aspect of the invention is an angiographic vascular occlusion agent comprising platelet-rich plasma and a biocompatible polymer.

Still another aspect of the invention is an angiographic vascular occlusion agent comprising a biocompatible polymer selected from the group consisting of alginate, chitosan, poly-L-lysine and a platelet-rich plasma concentrate.

Still yet another aspect of the invention is an angiographic vascular occlusion agent comprising platelet-rich plasma and sodium alginate, potassium alginate, barium alginate, magnesium alginate or any other alginate or a mixture thereof.

Still yet another aspect of the invention is an angiographic vascular occlusion agent comprising platelet-rich plasma and sodium alginate.

Still yet another aspect of the invention is an angiographic vascular occlusion agent comprising platelet-rich plasma and a chitosan.

Still yet another aspect of the invention is an angiographic vascular occlusion agent comprising platelet-rich plasma and a chitosan, chitosan-polyamine or preferably chitosan-cationic.

Still yet another aspect of the invention is an angiographic vascular occlusion agent comprising platelet-rich plasma and poly-L-lysine, poly-L-arginine, poly-L-glutamic acid, poly-L-histidine, poly-α-D-glutamic acid or a mixture thereof.

Still yet another aspect of the invention is an angiographic vascular occlusion agent comprising platelet-rich plasma and poly-L-lysine.

Still yet another aspect of the invention is an angiographic vascular occlusion agent which forms in situ an occlusion plug or clot proximal to, distal to and at a site of bleeding where to occlusion is desired.

Still another aspect of the invention is a method for angiographic vascular occlusion comprising an injection of a liquid biocompatible polymer with or without a platelet-rich plasma concentrate to a site proximate to, distal to and the site of bleeding.

DEFINITIONS

Figure 1:
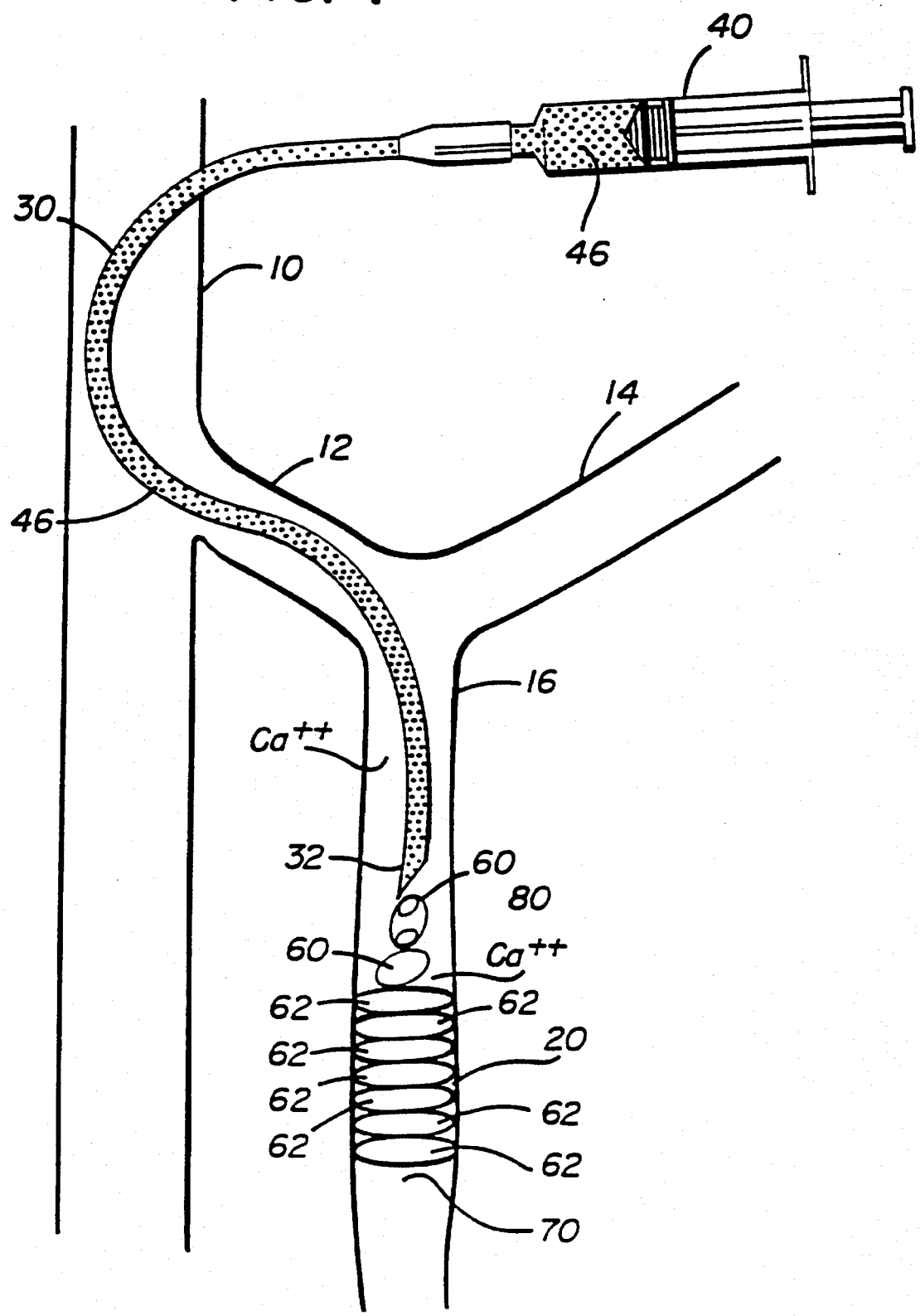
FIG. 1 is a schematic illustration of vascular occlusion.
Figure 2:
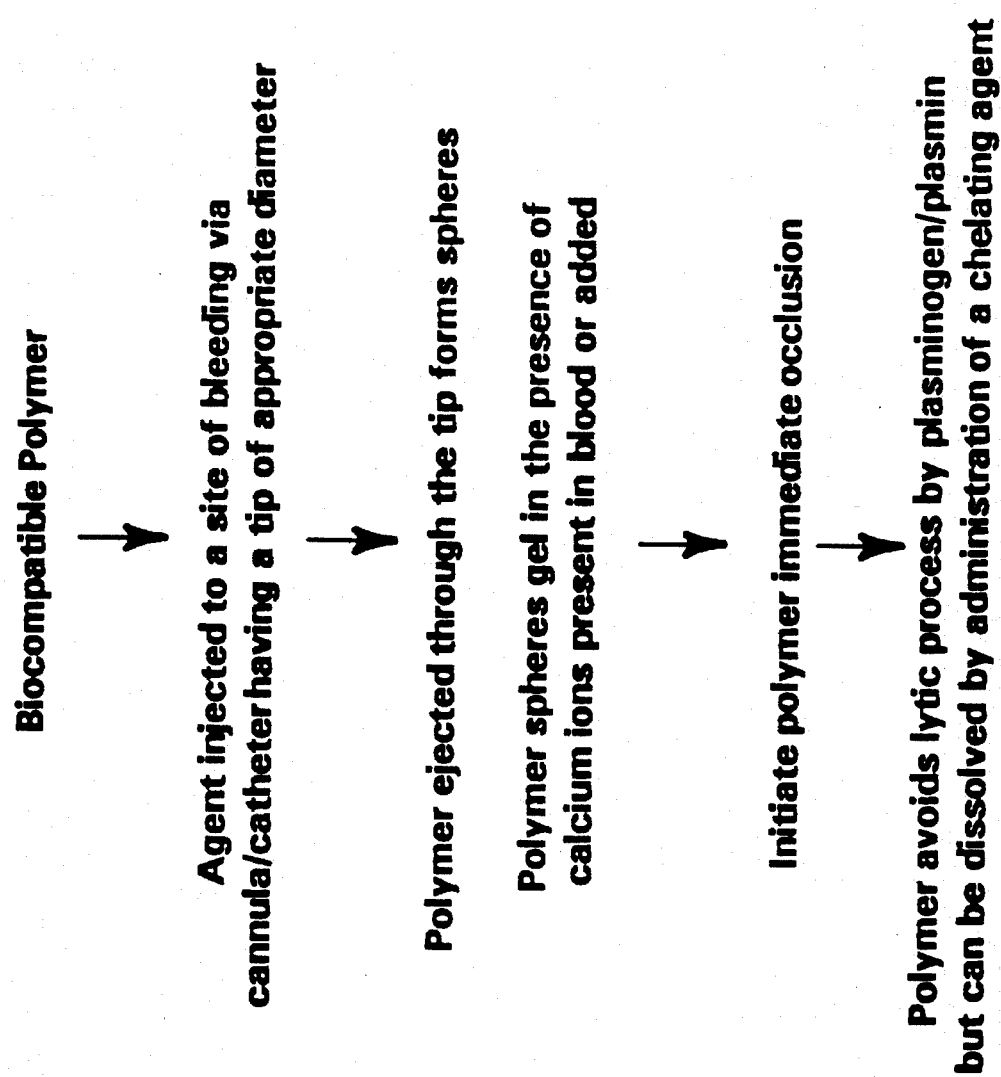
FIG. 2 is a scheme illustrating a vascular occlusion using a polymer occlusion agent.
Figure 3:
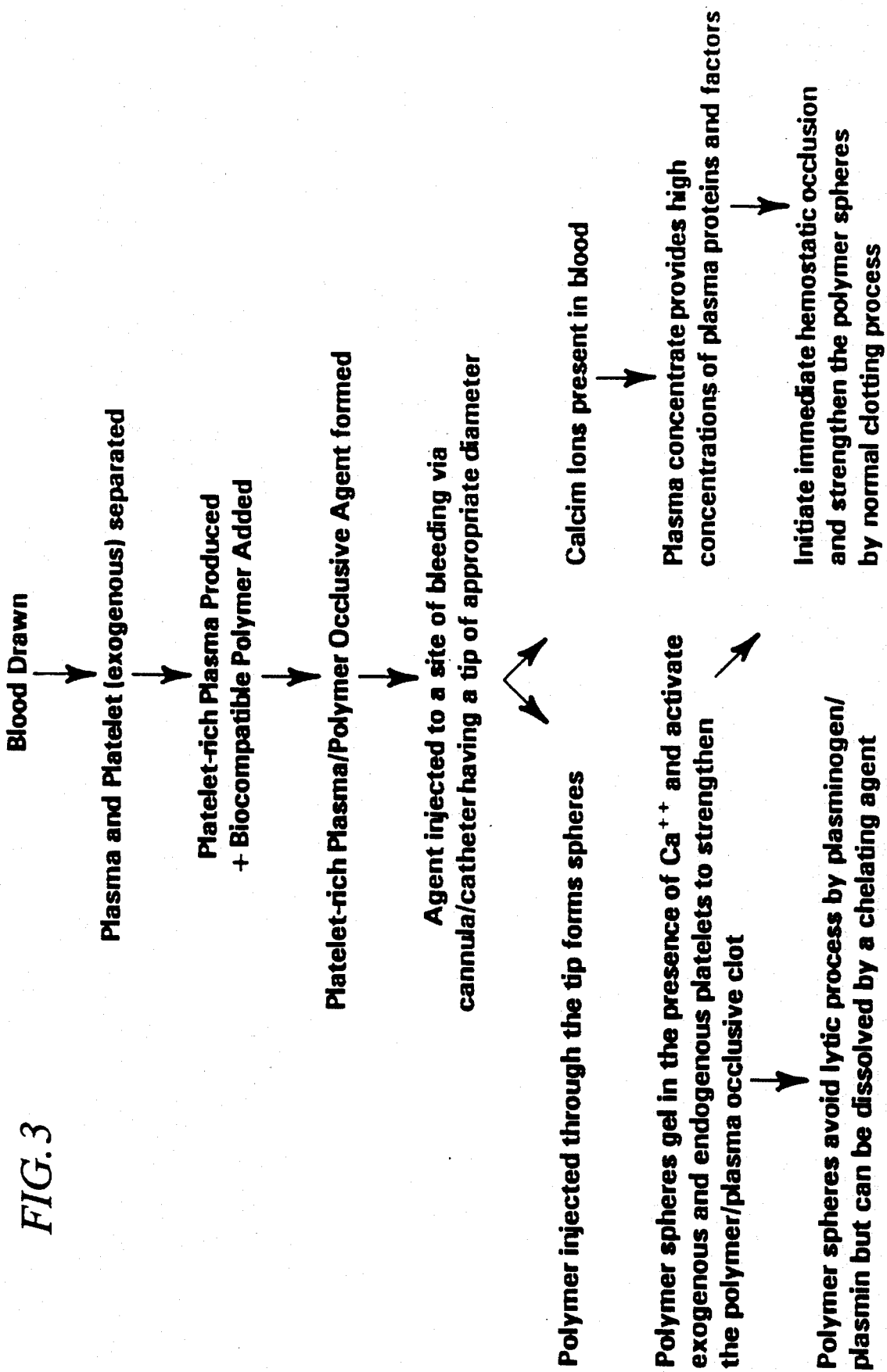
FIG. 3 is a scheme illustrating a semi-permanent vascular occlusion by using a combination of a biocompatible polymer with platelet-rich plasma.

As used herein:

"Biocompatible polymer" means any polymer physiologically acceptable to human and animal organisms, which is approved for the use in humans by the Federal Drug Administration. Examples of such polymers are alginates, potassium alginate, strontium alginate, barium alginate, magnesium alginate or any other alginate or a mixture thereof, chitin, chitosan, chitosan-polyamine or chitosan-cationic, or poly-L-amino acids, such as poly-L-lysine, poly-L-arginine, poly-L-glutamic acid, poly-L-histidine, poly-α-D-glutamic acid or a mixture thereof.

"Platelet-rich plasma" means concentrated plasm" containing the same volume of platelets which would be present in the normal volume of plasma before its concentration.

"Concentrated plasma" means normal plasma obtained by any means typically used for separating plasma from other blood components, concentrated 5 to 10 times of its original volume. The concentrated plasma thus contains 5–10 times smaller volume and the same amount of plasma proteins which are present in the normal nonconcentrated volume.

"Cascade-like effect" means a sequence of reactions beginning with applying the angiographic vascular occlusion agent to the vessel where the polymer quickly gels into a polymer plug or clot which triggers release of factors Va and Xa and thromboplastins from the exogenous platelets present in the platelet-rich plasma. These exogenous platelets release thromboplastins thereby initiating the physiological clotting process. Since the polymer is not a natural substrate for plasmin/plasminogen lytic reactions, the hemostatic occlusion continues unabated until the administration of the polymer is stopped or until the polymer is dissolved.

"Exogenous platelets" are platelets present in the platelet-rich plasma concentrate.

"Endogenous platelets" are platelets present in the circulating blood of the patient.

"Permanent occlusion" means occlusion which permanently blocks the vessel, fistula, ulcer, lesion or any other undesirable opening which needs permanent closure for more than a year or infinitely. The permanent occlusion will permanently eliminate the function of the vessel, or permanently seal the fistula, ulcer or lesion opening. The permanent occlusion is in the form of a permanent gel sphere plug. One example of permanent occlusion is the permanent occlusion of varicose veins. In certain instances, the permanent occlusion can be reversed by administration chelating agents as described below.

"Semi-permanent occlusion" or "temporary occlusion" means occlusion which blocks the vessel, fistula, ulcer, lesion or any other opening for several days to several weeks or even months. Such occlusion is used in sites where the healing process requires temporary stoppage of bleeding or secretion but which requires that after the healing, the occlusion plug is eliminated or removed. One example of semi-permanent occlusion is the occlusion of esophageal ulcer where the occlusion is not necessary after the ulcer heals.

DETAILED DESCRIPTION OF THE INVENTION

The current invention concerns two novel types of angiographic vascular occlusion agents. These occlusion agents are prepared from and contain physiologically acceptable biocompatible polymers alone (type 1) or in a combination with platelet-rich plasma concentrate (type 2). Biopolymers alone form a permanent occlusion. The combination of a biopolymer and platelet-rich plasma concentrate forms a temporary or semi-permanent vascular occlusion. Both permanent or semi-permanent occlusion is reversible according to the invention.

I. Angiographic Vascular Occlusion Agents of the Invention

The angiographic vascular occlusion agents of the invention are typically prepared from a physiologically biocompatible acceptable polymer alone or in combination with platelet-rich plasma. Occluding agent according to the invention is based on the inherent property of the polymer of the invention to gel upon contact with divalent cations. Gelled polymer provides rapid hemostasis or occlusion by the formed gel sphere or plug formed of gel spheres strengthened by fibrin fibers.

These agents are typically administered by intravenously inserted catheter or cannula which is introduced into an a proximity of the bleeding, rupture, fistula, ulcer or lesion. The agents are administered in the liquid form through a cannula or catheter having a tip of a diameter corresponding roughly to a size of a vessel, opening or lesion. The liquid agent is injected through the cannula/catheter tip. Upon ejection of a droplet from the needle tip the liquid agent gels and forms a polymer sphere which occludes the vessel, ulcer, fistula, lesion or any other bleeding or secretion opening. The vessel or the opening is occluded with the gelled biopolymer-clot plug, and in this way, bleeding or secretion is stopped and/or occlusion is achieved. Some emboli are permanent and others are temporary or semi-permanent, depending on the occlusion agent used.

The occlusion of a vessel bleeding according to the invention is schematically illustrated in FIG. 1. FIG. 1 shows a large blood vessel (10) which branches into smaller (12) and smaller vessels (14 and 16). The site of bleeding (20) is shown in one of the branches (16). The surgical angiographic catheter (30) is preferably made of polyethylene, nylon, silicon or any other suitable material, of the diameter smaller than the vessel (16) diameter. The end of the catheter or cannula tip (32) is conically shaped to allow drop formation, or the needle is inserted into the catheter. The catheter is filled with the liquid biopolymer (46) or with a liquid polymer platelet rich plasma combination. When the pressure is exerted through a syringe (40) or any droplet generator apparatus, drops (60) of liquid biopolymer (60) are ejected from the needle or the cannula/catheter tip (32), where, upon contact with $Ca^{++}$ ions they form gelled spheres (62) of the size of the vessel or opening. In the case of the vessel, the tip of the needle is inserted proximally from the bleeding site (70) and droplets are ejected continually so that they occlude the vessel proximally from the bleeding, continuing toward the bleeding, and occluding the bleeding site. The occlusion of the vessel is continued until occlusion occurs also distally (80) of the bleeding site, as seen in FIG. 1, for example, by gentle pulling out the catheter so that the gelled spheres occlude the vessel by plugging it proximally (70) and distally (80) of the bleeding site.

1. Type 1 Vascular Occlusion Agent Containing a Biopolymer

An angiographic occlusion agent type 1 contains a physiologically acceptable biocompatible polymer which gels with a change in temperature or upon contact with calcium or other divalent cations forming a polymer gel sphere. The biopolymer component of the angiographic vascular occlusion agent is selected from the group consisting of alginates, chitosans and poly-L-amino acids or a mixture thereof. The any other requirement for the polymer is that it must gel upon contact with calcium or other divalent cations or anions.

A. Type-1 Occlusion Agents

The alginate polymer, such as sodium alginate, calcium alginate, strontium alginate, barium alginate, magnesium alginate or any other alginate or a mixture thereof, is added to the platelet-rich plasma concentrate in concentration from 0.001% to about 20%, preferably from about 0.1% about 10%.

In alternative, the polymer is selected from the group consisting of poly-L-amino acids, such as poly-L-lysine, poly-L-arginine, poly-L-glutamic acid, poly-L-histidine, poly-α-D-glutamic acid or a mixture thereof. This poly-L-amino acid polymer is added in concentration from about 0.001% to about 30%, preferably from about 0.1% to about 15%.

In still another alternative, the polymer may be chitosan or chitin, such as chitosan-polyamine or preferably chitosan-cationic, which forms strong and clear films and gels when brought in contact with divalent cations. These polymers are biodegradable and non-toxic. Chitosan is added in concentration from about 0.1% to about 10%. Addition of chitosan accelerates wound healing and having by itself certain bioadhesive properties, increases adhesivity of the chitosan gel spheres to a vessel wall.

The polymer is dissolved in small volume, about 0.5–1 ml, of saline or sterile water and used as is or various pharmaceutically acceptable additives may be added.

B. Type-1 Agents-Mode of Administration

Type-1 vascular occlusion agent is administered in three alternate ways. First, the solution of the biopolymer from about 0.001 to about 30%, preferably about 1–10%, of the biopolymer is dissolved in the sterile water or saline, solution is sterilized and injected as is. This route of occlusion is particularly suitable for permanent occlusion of small vessels where the circulating blood contains enough calcium ions to gel the polymer. The polymer gel spheres form on site and upon mechanical contact with the vessel walls and in the presence of calcium ions, it forms spheres of the same size as is the diameter of the vessel to be occluded. Because it is injected as a liquid, polymer forms gelled spheres sufficiently large to occlude small vessels without addition of exogenous calcium ions.

For larger vessels, where the endogenous concentration of calcium ions may not be sufficient to gel the amount of administered polymer, the second mode of the biopolymer administration is used. In this case, the biopolymer is formulated in solution from about 0.001 to about 30%, preferably from 1–10%, as above, except that the solution is ejected from the catheter and dropped into the solution of 1–3%, preferably about 1.7%, of calcium chloride. In this case, the polymer spheres are formed in the calcium solution and are then injected through the catheter or cannula to the proximity of the bleeding. Because these spheres are formed of the gelled polymer, they are pliable and easily injectable through the catheter because they can change their diameter and shape to conform to a diameter of the cannula or catheter. Thus, the formed spheres elongate and conform to the catheter diameter during injection. Once they are at a site of occlusion, they regain their previous sphere shape. The formed spheres by this method can have sizes from about 0.1 to about 5 mm, depending on the intended use and on the size of the syringe needle tip or the catheter/cannula opening aperture.

The third mode of administration of the biopolymer and formation of occlusive spheres is by dissolving the biopolymer in a solution of about 0.1% of calcium solution when the polymer does not yet gel or, as in the first instance, in the saline or sterile water and is injected in the liquid form to the site where the occlusion is needed and the calcium solution is independently added before, during or after the injection of the biopolymer.

In this way, the complete permanent occlusion of the vessels is achieved.

C. Reversible Permanent Occlusion

One of the advantages of the current invention is that the permanent occlusion can be, upon will, reversed and the occlusive biopolymer plug can be dissolved by administering physiologically acceptable nonharmful chelating agents in amount sufficient to dissolve the polymer plug.

Examples of such chelating agents are citrate, tartrate, ethylenediaminetetraacetic acid (EDTA), EDTA salts, such as sodium EDTA, dimercaptol, penicillamine, deferoxamine, dithizone, cisplastin, chlorophyll and other such chelating agents. These agents are easily administered dissolved in distilled water, sterile water, saline, buffers, etc., to a site where the permanent occlusion was previously induced. Details for the method of dissolution are to be found in the co-pending patent application Ser. No. 08/207,937 filed on Mar. 8, 1994.

2. Type 2-occlusive agent Containing a Biopolymer in Combination with a Platelet-Rich Plasma An angiographic occlusion agent type 2 contains a physiologically acceptable biocompatible polymer in combination with platelet-rich plasma. Biocompatible polymer gels with a change in temperature or upon contact with calcium or other divalent cations, forming a polymer gel sphere clot with platelet-rich plasma concentrate containing a 5–10 times higher concentration of fibrinogen and other plasma proteins than is the normal concentration of these components in nonconcentrated normal plasma. In this type of occlusive agents, the biopolymer gels upon contact with calcium ions, forming a gelled sphere. The combination of plasma concentrate and platelets present in the occlusion agent promotes rapid clotting. The polymer, additionally, causes activation and aggregation of both exogenous and endogenous platelets and thereby induces and increases formation of occlusive sphere clot in a cascade-like manner.

Type 2 occlusion agent are temporary or semi-permanent in nature depending on the proportionate liquid composition of the biopolymer plasma concentrate. The higher the ratio of the polymer to concentrated plasma, the more permanent the occlusion is. When the concentration of the biopolymer to concentrated plasma is around 20–30%, the formed occlusion plug is semi-permanent and lasts for several weeks to months. It can be, of course, always reversibly removed by using a dissolution step, as described in section C above. When the concentration of the biopolymer is around 0.001 to about 3%, the formed plug is temporary and the blood typically recanalize within a few hours or days through the formed occlusion plug. Typically, at that time, the bleeding is stopped, and the temporary occlusion fulfilled its function. This approach is used in small bleeding wounds, punctures or tiny fistulas where the rapid occlusion is needed but where the bleeding responds to the normal coagulation processes including the healing effect of platelets.

Chitosan and poly-L-lysine may have additional advantages due to their ability to inhibit bleeding independent of normal coagulation factors. Both chitosan and poly-L-lysine have high charge (positive) density. These high density positive charges form a coagulum upon contact with erythrocytes and fibrinogen. Erythrocytes and fibrinogen have high density negative charges on their surface which combine (cross-link) with the positive charges on the polymers to rapidly form a coagulum. In addition, chitosan and poly-L-lysine can repolymerize (gel) when exposed to single and multivalent anions. This is important when normal clotting factors are compromised which is often the case in patients with for example gastrointestinal bleeding due to transfusion.

A. Type 2-Occlusion Agents Containing a Biopolymer in Combination with Platelet-Rich Plasma Type 2 occlusion agents contains a biopolymer in combination with platelet-rich plasma.

Typically, the polymer is selected from the group consisting of an alginate, chitosan and poly-L-amino acids.

The alginate polymer, such as sodium alginate, calcium alginate, strontium alginate, barium alginate, magnesium alginate or any other alginate or a mixture thereof, is added to the platelet-rich plasma concentrate in concentration from 0.001% to about 20%, preferably from about 0.1% about 10%.

In alternative, the polymer is selected from the group consisting of poly-L-amino acids, such as poly-L-lysine, poly-L-arginine, poly-L-glutamic acid, poly-L-histidine, poly-α-D-glutamic acid or a mixture thereof. This poly-L-amino acid polymer is added in concentration from about 0.001% to about 30%, preferably from about 0.1% to about 1% volume per volume of concentrated plasma.

In still another alternative, the polymer may be chitosan or chitin, such as chitosan-polyamine or preferably chitosan-cationic, which forms strong and clear films and gels when brought in contact with divalent cations. These polymers are biodegradable and non-toxic. Chitosan is added in concentration from about 0.1% to about 10%. Addition of chitosan accelerates wound healing and having by itself certain bioadhesive properties, increases adhesivity of the platelet rich plasma-chitosan hemostatic adhesive.

The polymer is dissolved in small volume, about 0.5–1 ml, of concentrated plasma and then added to the platelet-rich plasma.

In its most preferred form, the angiographic vascular occlusion agent type-2 is autologous, that is, the concentrated plasma is prepared from the patient's own blood and combined with a physiologically acceptable biocompatible polymer. The angiographic occlusive agent of the invention is preferably prepared in the operating room at the time of surgery. The permanent occlusive plasma/polymer agent has a low platelet-rich plasma to polymer ratio. Generally, the agent is composed of about 0.001% to 3% concentrated, preferably autologous platelet-rich plasma and from about 97% to about 99.999% of the polymer.

For more temporary occlusion, the ratio polymer to concentrated plasma is increased from 3% to about 10%. In this instance, the occlusion agent is composed of 3–10% of biopolymer and 90–97% of concentrated plasma. These agents typically occlude the vessel for 2–8 weeks. Semi-permanent occlusion agents are formed of 10–30% preferably 20% of biopolymer and 70–90% of concentrated plasma. These agents typically occlude the vessel or other opening semi-permanently for 4–16 weeks or longer. These semi-permanent agents are particularly useful for occlusion of ulcer or ulcerous tissue where there is a slow healing process.

When mixed and injected, as described above, into a bleeding vessel or site where occlusion is necessary, the polymer component gels quickly with a change in temperature or upon contact with endogenous or exogenous calcium present in plasma concentrate or other divalent cations. When the polymer gels it aggregates and activates the exogenous and endogenous platelets. Activated platelets release thromboplastin. The gelled polymer forms the initial occlusive polymer clot quickly strengthened with fibrinogen fibers within which the platelets or platelets debris is/are caught. The exogenous platelet activation by polymer initiates and enhances the normal physiological clotting system much faster than under normal circumstances and the clot develops further in the presence of endogenous $Ca^{++}$, plasma factors V and X, which are present in a concentrated form in plasma concentrate, converting prothrombin to thrombin. Meanwhile, the gelled polymer activates more and more exogenous and endogenous platelets in a cascade-like fashion, enlarges and strengthens the original polymer clot and forms a clot matrix. Such clot matrix is formed after the activation of platelets leading to activation of prothrombin to thrombin, activation of fibrinogen by thrombin, conversion of fibrinogen to initial fibrin monomers, formation of the weak fibrin clot and strengthening of fibrin by cross-linking with factor XIIIa. The autologous thrombin thus formed in response to the platelet activation then converts soluble fibrinogen to a stable fibrin clot in the presence of factor XIIIa, a fibrin stabilizing factor, that catalyzes formation of peptide bonds between fibrin molecules and in this way stabilizes the clot.

Gelling polymer acts as an extraneous impulse activating both exogenously supplied and endogenous platelets. A large volume of exogenous platelets is present in the platelet-rich plasma concentrate. Utilizing the high concentrations of plasma proteins, prothrombin, fibrinogen, and clotting factors present in the platelet-rich plasma concentrate, the physiological clotting begins and on a large scale, having already present and available all necessary clotting factors and components.

Gelled polymer which forms the initial clot is now substantially strengthened by platelets and platelet debris and its adhesivity is enhanced by the natural clotting processes. Meanwhile, the polymer activates more and more platelets in a cascade-like fashion so that the size and strength of the clot are much larger than the normal clot.

Since the natural coagulation is endogenously regulated and controlled and is subject to lysis, as described above, such regulation mechanisms limit the formation of a normal clot to 3–5 minutes. After that time the strength of a normal clot cannot be increased. On the other hand, the polymer is not subject to lysis or any other regulatory mechanisms and the formation of the occlusion clot can therefore proceed unhindered.

B. Type 2-Agents—Mode of Administration

Using the current invention, the platelet-rich plasma is prepared as described below and in examples. The chosen polymer selected from those described above is then added and the agent is injected through the catheter or cannula into the vicinity of the bleeding vessel, fistula, ulcer or lesion. Calcium is either endogenously present or a solution containing calcium or other divalent cations is added as described in the section I. Such solution causes gelling of the polymer.

Type-2 vascular occlusion agent is administered in three alternate ways. First, the solution of the biopolymer from about 0.001–30% preferably about 20%, of the biopolymer is dissolved in the sterile water, solution is sterilized, concentrated plasma (70–99.9%) and is added and injected as is according to FIG. 1. This route of occlusion is particularly suitable for temporary or semi-permanent occlusion of small vessels where the circulating blood and concentrated plasma contain enough calcium ions to gel the polymer. The polymer gel spheres form on site and upon mechanical contact with the vessel walls and in the presence of calcium ions. The polymer forms spheres of the same size as is the diameter of the vessel. Presence of concentrated plasma in the type-2 agent additionally provides strengthening properties of the gel sphere clot, triggering the endogenous clotting process and forming rapidly polymer gel-fibrin fiber occlusive clot which adheres to the walls surrounding the bleeding site and in this way contains bleeding or secretion from the place when the occlusion is needed.

For large vessels, where the endogenous concentration of calcium ions may not be sufficient to form gel spheres sufficiently large to occlude such vessel, the second mode of the type 2 occlusive agent administration is used. In this case, the biopolymer is formulated in a solution, as above, except that the solution is dropped into the solution of 1–3%, preferably about 1.7% of calcium chloride. In this case, the polymer spheres are formed in the calcium solution, concentrated plasma is added and mixed with the polymer spheres and thus formed type 2 occlusion agent is then injected through the catheter or cannula to the proximity of the bleeding. The formed spheres by this method can have sizes from about 0.1 to about 1 mm. In combination with concentrated plasma they can form occlusion plugs in range from about 1 mm to about 5 mm, depending on the intended use.

The preformed spheres are then injected through the catheter as seen in FIG. 1. In this instant, however, the occlusion is not necessarily by making the spheres to conform to a site of the vessel or the opening to be occluded. In this instance, the presence of concentrated plasma provide a mechanism for formation of a fibrin fibers material in which the spheres are embedded forming one large mesh of the fibrin matrix-spheres-platelets. This mesh then acts as the occlusion agent. As pointed out above, in this instance, depending on the amount of polymer, or on the number of gelled spheres, the occlusion may be temporary, allowing recanalization, or more or less semi-permanent, allowing slow or almost none recanalization through the mesh. As in previous instances, the polymer component of the mesh can be dissolved upon will by steps as described in section I C above. The fibrin mesh will be sooner or later lysed by plasmin/plasminogen mechanism, as described below.

The third mode of administration of the biopolymer and formation of occlusive spheres is by dissolving the biopolymer in a solution of about 0.1% of calcium solution before the concentrated plasma is added. The calcium solution can alternatively be independently added before, during or after the injection of the biopolymer concentrated plasma agent.

In this way, the temporary or semi-permanent occlusion of the vessels is achieved.

Under normal physiological circumstances, regulatory mechanisms are present that prevent activated coagulation reactions from proceeding unchecked beyond and behind hemostasis, which could cause either local thrombosis or disseminated intravascular coagulation. These regulatory mechanisms include fibrinolytic system, cellular clearance of activated clotting factors, and neutralization within the blood of the enzymes and activated cofactors of coagulation.

The fibrinolytic system activates fibrin deposition. By dissolving fibrin, this system helps keep open the lumen of an injured blood vessel and presents formation of thrombin. A balance between fibrin deposition and lysis maintains and remolds the hemostatic seal during the days required to repair the injured vessel wall. This system is directly active in removal of fibrin mesh and in assuring that the occlusion is only temporary or semi-permanent.

When fibrinogen is converted to fibrin, lysine residues become available on the molecule to which plasminogen can bind tightly by way of special sites on plasminogen called lysine binding sites. Plasminogen activators triggering lysis of intravascularly deposited fibrin are released from vascular endothelial cells. These regulatory mechanisms are very important for reversibility of the occlusive hemostasis according to the invention when the occlusion is temporary or semi-permanent.

For both type 1 and type 2 agents mechanisms of occlusion or mode of administration can be as described above or by any modification, combination or alteration of conditions which would become apparent from the describe modes of action.

II. Method of Preparation of Occlusive Agents

A. Type-1 Occlusion Agents

Type 1 occlusive agents are prepared by dissolving the biopolymer in a sterile water, saline or saline solution optionally containing divalent cations, depending on the mode of administration.

Typically, the alginate biopolymer is first selected from the groups consisting of alginates, poly-L-amino acids or chitosans. Alginates, such as sodium alginate, calcium alginate, potassium alginate, strontium alginate, barium alginate, magnesium alginate or any other alginate or a mixture thereof, are obtained from Protan (Pronova MVG).

Poly-L-amino acids, such as poly-L-lysine, poly-L-arginine, poly-L-glutamic acid, poly-L-histidine, poly-α-D-glutamic acid or a mixture thereof are obtained from Sigma, St. Louis, Mo.

Chitosans, such as chitosan polyamine, chitosan-cationic or chitin are the biodegradable non-toxic natural polymer which is the natural structure components of shellfish, crab, shrimp and lobster. Chitin or chitosan are commercially available from Protan. Chitosan, particularly its anionic polymers, form gels and coagulate proteins. As the occlusion agent, it is used alone in concentration form 0.001 to about 3%. Chitosan is soluble in 0.2% acetic acid aqueous solution or organic solvents.

For the purposes of the occlusion, 0.001–3 g of biopolymers named above are dissolved in 1-000 ml of a sterile water, saline, or in a solution containing 1–3%, preferably 1.7%, divalent cations, preferably calcium chloride. The biopolymer is dissolved before use. Typically, the biopolymer is stored in a dry form in a preweighed amount in a sterile vial. Depending on the occlusion type and extent of bleeding, the sterile water, saline or calcium chloride containing solution is added in amount to prepare biopolymer solution having desired concentration as above. The solution is properly mixed and injected via the catheter to a site of bleeding or injury where the occlusion is needed.

B. Type-2 Occlusion Agents

Type-2 occlusion agents comprise a biologically acceptable polymer in combination with the platelet-rich plasma.

Preparation of Platelet-Rich Plasma

Platelet-rich plasma is prepared from the full blood either of the patient to be treated (autologous plasma) or from human plasma from persons other than the patient (non-autologous plasma). In the latter case, care is taken to utilize only healthy and non-contaminated full blood. Additionally, in the case of planned surgery, the patient may provide his blood before the operation so that the concentrated plasma is prepared in advance. In the case of acute injuries or trauma, the angiographic vascular occlusion agent according to the invention is prepared at the time of operation or treatment. Thus, no blood bank, storage, prior collection of blood or isolated platelets is necessary, although the occlusive agent may be prepared from the blood available from the blood bank if necessary. The current occlusive agent thus can be prepared without any danger that the patient may encounter immune reaction or become infected with the another person's blood.

The angiographic vascular occlusion agent is prepared from full blood by separating red blood cells from plasma and by isolating and separating isolated platelets. Typically, full blood is drawn into a buffered anticoagulant agent, such as sodium citrate, and centrifuged to separate platelets and plasma from the red blood cells. Plasma is removed and centrifuged for the second time at high speed to separate the platelets and the plasma. Plasma is again removed and concentrated by a factor of 5–10 preferably by a factor of about 7–8 by using any means suitable for concentration, preferably by filtration and/or using a vacuum. Platelets precipitate is saved separately and ultimately added to the plasma concentrate.

Typically, platelets isolated from the volume of the plasma prior to its concentration are added to the mixture of the concentrated plasma. The platelets to plasma ratio is from 1:2 to 2:1 preferably about 1:1 before plasma concentration.

A polymer selected from the group of alginates, chitosans and poly-L-amino acids or a mixture thereof is added.

The angiographic vascular occlusion agent of the invention is prepared by mixing together the concentrated plasma, isolated platelets and the polymer. The polymer is dissolved in small volume, about 0.5–1 ml, of concentrated plasma and then added to the platelet-rich plasma. Polymer is added to the platelet-rich plasma concentrate in concentration from 70% to about 99.99% forming a mixture of the platelet-rich plasma concentrate and polymer. Concentrated plasma contains all plasma proteins, in concentration levels at which they are normally present in the plasma. These proteins are fibrinogen (factor I), prothrombin (factor II), and other plasma coagulation factors as described above.

The mixture of the platelet-rich plasma and polymer forms the angiographic vascular occlusion agent of the invention. The agent may additionally contain other therapeutically active pharmaceutically acceptable agents or pharmaceutically acceptable additives such as antibiotics, steroids, vasopressin, hormones, chemotherapeutic agents, and growth factors.

The type-2 agent of the invention is able to occlude a bleeding vessel without the addition of exogenous thrombin or any other agent. The bleeding wound typically provides sufficient amount of calcium to gel the polymer, typically added in 1%–20%, preferably 10%. The occlusion agent is injected via the catheter to the vessel or tissue where the wound, incision, cut, bleeding surface, fistula, ulcer o other injury occurs. In these cases, the presence of the polymer which gels into polymer spheres forms the initial occlusion emboli. The occlusion is enhanced by the coagulation activity of platelets and their normal hemostatic properties. The presence of exogenous platelets and high concentrations of available plasma proteins needed for coagulation allows rapid hemostatic action and clotting build-up on and over the polymer occlusion emboli.

While it is preferred that the autologous platelet-rich plasma is used whenever possible, the non-autologous platelet-rich plasma from other humans is equally useful and is prepared by the same process and under the same conditions.

The angiographic vascular occlusion agents containing platelet-rich plasma and polymers provide quick occlusion due to the presence of the polymer which, as one of its own properties, gels upon contact with calcium or other divalent cations and as a foreign substance, causes aggregation and clotting of exogenous and endogenous platelets. The clotting formation and adhesive strength of the agent is fast.

The process for preparation of the angiographic vascular occlusion agent is fast. Typically the occlusion agent can be produced within 2–15 minutes and does not require any special equipment, agents or procedures than those used in the biochemical medical laboratory on a daily basis.

When the occlusion agent type-2 is prepared in advance, essentially the same procedure is followed except that the plasma concentrate and platelets are stored separately in the refrigerator, if the agent will be used within 24 hours, or in the freezer, if it will be used later. Polymer is stored and preweighed in the desired amount, preferably in amount which would provide 70%–99% dilution with plasma concentrate. The volume of the angiographic occlusion agent depends on the extent of the surgery. Typically, platelet-rich plasma concentrate is obtained from 30 ml blood, which provides about 1.5–2.5 ml of concentrate. If the vessel is large, an appropriately larger volume of concentrate is prepared. In practice of the invention, before the occlusion agents of the invention are applied, a source of bleeding, secretion or site of injury, fistula, ulcer or lesion, is first located by for example, selective angiography, or contrasting media. Then, the rate of bleeding or site of the opening is determined by, for example, selective arteriography and X-rays. After the site of bleeding, secretion, fistula, ulcer or other lesion is detected, the occlusive agent is selected from type-1 for permanent occlusion for type-2 for temporary or semi-permanent occlusion. Then the agent is prepared in the concentration needed to achieve complete occlusion, catheter or cannula is filed with the occlusion agent and inserted to a close proximity of the occlusion site. In a vessel, as discussed above, the tip of the catheter is first inserted proximally from the site of bleeding and slowly pulled out so that the occlusion plug is formed around the bleeding site as well as distally from it.

UTILITY

The angiographic vascular occlusion agents according to the invention have many advantages over other currently available occlusive agents. They provide controllable, reversible, permanent, temporary or semi-permanent occlusion. The presence of the polymer in the occlusion agent allows a formation of the occlusive clot. The clot size and strength in type-1 agents is controlled by the amount of biopolymer injected, by the mode of biopolymer administration and by the size of the vessel or other opening to be occluded. In type-2 agent, the action is further magnified by the presence of platelet-rich plasma acting in a cascade-like manner.

It is one of the advantages of the invention that the treating surgeon or physician can determine which type of occlusion is needed and what volume is necessary to achieve the complete occlusion. Also, should the bleeding not be contained or occlusion achieved by the available volume of the agent, the additional volume can be quickly and conveniently prepared.

Another advantage of the autologous occlusive agent is the absence of foreign proteins, such as bovine and human fibrinogen or thrombin which may lead to immune reactions. The reduced risk of transmission of infectious and parasitic diseases, such as HIV and hepatitis, is also a major advantage of the occlusive agents of the invention because if there is no time to test the donor's blood for these diseases, these new occlusive agents may be prepared from the patient's own blood in the operating room before use or the type 1 occlusive agent may be used.

The angiographic vascular occlusion agent of the invention is advantageously used for treating defects or injuries such as esophageal arterial and gastric mucosal bleeding, recurrent ulceration bleeding, small-bowel bleeding, colonic bleeding, bleeding due to angiodysplasia of the colon, any postoperative bleeding, and other gastrointestinal bleeding, pelvic bleeding, vaginal bleeding, internal iliac artery bleeding, pancreatic or renal bleeding, hepatic or splenic bleeding, thoracic bleeding and hemoptysis, head, neck or extremity bleeding. Additionally, selective embolization according to the invention can be used for embolization of varicose veins, as well as to stop variceal bleeding, and to achieve selective embolization of gastric and esophageal varices. The current invention is also suitable for vascular occlusion of vascular tumors, for palliative embolic obliteration of tumor vascularity, embolization of renal cell carcinoma as well as for embolization of arteriovenous malformations, pulmonary arteriovenous malformations, solid organ arteriovenous malformations, for carotid cavernous fistulae and also for embolic therapy for organ ablation to reduce, for example, abnormal endocrine function by embolizing adrenal and parathyroid tumors.

Embolic therapy is the method of choice for treating bleeding duodenal ulcers and bleeding from branches of the left gastric artery.

In addition, the hemorrhage from the vascular beds of the kidneys, liver, and pelvis which do not respond to vasopression, is best treated by selective embolization. Renal hemorrhage secondary to trauma or tumor can be successfully treated with selective embolization.

Embolization of thoracic intercostal arteries can be used to control hemorrhage in breast carcinoma and trauma. Hemoptysis can be controlled in cystic fibrosis, tuberculosis and bronchiectasis by embolization. Epistaxis and hemorrhage resulting from head and neck tumors can be treated by embolization of the branches of the external carotid arteries. Esophageal varices can be obliterated by embolic therapy.

Preoperative embolization of vascular tumors (renal, meningiomas and juvenile angiofibromas) reduces blood loss during surgery. In addition to preventing blood loss during surgical removal of renal tumors, diminished seeding of metastases may be beneficial. Selective embolization also is applicable in areas such as arteriovenous malformations and fistula in solid organs such as the liver and kidney.

The treatment may be used alone or in combination with other techniques and drugs typically used to correct these problems.

A major difference between these angiographic vascular occlusion agents and previous embolic agents is the use of gelled polymer as the main occlusive component and, in type 2 agent, inclusion of living, metabolizing platelets, high concentration of plasma proteins in the presence of the polymer. The importance of platelets in thrombosis is increasingly recognized. For example, platelets contain a vast number of biologically active molecules within cytoplasmic granules. The possible therapeutic effect arising from the fact the exogenous platelets and particularly autologous platelets are present in the angiographic vascular occlusion agent type 2 is therefore an additional advantage of the invention.

The following examples are intended to illustrate the invention and its utility. These examples are not to be interpreted as limiting the invention in any way.

EXAMPLE 1

Use of Sodium Alginate Spheres as a Permanent Angiographic Vascular Occlusion Agent This example illustrates the occlusive effect of the angiographic vascular occlusion agent type 1 in the permanent occlusion of the splenic vein.

Sodium alginate spheres were made by dropping 1% alginate (Protan Pronova MVG) saline solution into 1.7% $CaCl_2$. The resulting spheres (300–500μ) were rinsed in 6 mM $CaCl_2$ and maintained sterile until injection.

A 30 kg dog was anesthetized and the splenic vein was isolated. The spheres were injected retrograde into a branch of the splenic vein to occlude the vessel. The midline incision was closed and the dog was maintained for 21 days. The animal remained in good health. At 21 days, the animal was anesthetized and the splenic vein was occluded but appeared normal. All other splenic vessels remained patent. The animal was sacrificed and the occluded vessel was removed for histology. The tissue was prepared for H & E staining using standard histology methods. Histology showed little inflammation around the occlusive spheres. Fibrosis (2–10 cells) adhered the spheres to the vessel wall. No other pathology could be demonstrated in the histology.

EXAMPLE 2

Use of Chitosan as a Angiographic Vascular Occlusion Agent

This example illustrates the occlusive effect of the chitosan angiographic vascular occlusion agent on the kidney fistula.

Chitosan 1% (Protan) was dissolved in 100 ml of saline solution and 1% sodium alginate was added.

A 30 kg dog was anesthetized and the catheter was inserted into the branch of the renal artery where the fistula was localized. The dog was maintained and his renal function was followed. The animal remained in good health. The animal was anesthetized and kidney X-rays were taken showing that the artery was occluded but appeared normal at 30 days. All other renal vessels remained patent.

EXAMPLE 3

Use of Poly-L-Lysine as a Permanent Angiographic Vascular Occlusion Agent

This example illustrates the permanent occlusive effect of the poly-L-lysine angiographic vascular occlusion agent on the splenic vein.

Poly-L-lysine solution was prepared by dissolving 2 g of poly-L-lysine commercially available from Sigma Chemical company in 100 ml saline solution. One ml of the solution was injected into the splenic vein.

A 30 kg dog was anesthetized and the splenic vein was isolated. The poly-L-lysine were injected retrograde into a branch of the splenic vein to occlude the vessel. The midline incision was closed and the dog was maintained for 60 days. Through the study, the animal remained in good health. At 60 days post occlusion, the animal was anesthetized and the splenic vein was found to be occluded but appeared normal. All other splenic vessels remained functional. The animal was sacrificed and the occluded vessel was removed for histology. The tissue was prepared for H & E staining using standard histology methods. Histology showed the presence of occlusive polymer in the splenic vein. No recanalization or other pathology could be demonstrated in the histology.

EXAMPLE 4

Preparation of Autologous Plasma and Polymer Containing Occlusive Agent

This example illustrates preparation of occlusive platelet-rich plasma/alginate (type-2) containing hemostatic agent.

A 30 ml blood sample was drawn from a dog and placed into 0.1055M buffered sodium citrate solution. The tubes were centrifuged at 770×g for 3 minutes and a 15 ml platelet-rich plasma sample was removed. The plasma was centrifuged a second time at 2000×g. Then, the plasma was removed and the platelets were saved. The plasma was concentrated by centrifugation through a 30,000 MW cut off filter obtained from CentriCell Polysciences, Inc. for 20 minutes. The plasma was concentrated by a factor of 7–8, that is 270–390 mg of fibrinogen present in 100 ml of normal plasma was concentrated to >2000 mg/100 ml. Sodium alginate (0.2–3% in saline) obtained from Kelco Gel LV, Merck & Co., San Diego, Calif., was dissolved in 1 ml of the concentrated plasma. Plasma to polymer ratio was 1:1. The platelets obtained from the used equal volume of blood, that is from 30 ml of full blood were added back to the 4 ml of concentrated plasma and alginate. The mixture was stirred and used as an occlusive agent in the dog splenic study as in Example 3.

EXAMPLE 5

Preparation of Autologous Plasma and Polymer Containing Occlusive Agent

This example illustrates preparation of occlusive hemostatic platelet-rich plasma/chitosan containing type 2 agent.

A 30 ml blood sample was drawn from a dog and placed into 0.1055M buffered sodium citrate solution. The tubes were centrifuged at 770×g for 3 minutes and a 15 ml platelet-rich plasma sample was removed. The plasma was centrifuged a second time at 2000×g. Then, the plasma was removed and the platelets were saved. The plasma was concentrated by centrifugation through a 30,000 MW cut off filter obtained from CentriCell Polysciences, Inc. for 20 minutes. The plasma was concentrated by a factor of 7–8, that is 270–390 mg of fibrinogen present in 100 ml of normal plasma was concentrated to >2000 mg/100 ml. Sodium alginate (0.1–1%) obtained from Kelco Gel LV, Merck & Co., San Diego, Calif., was dissolved in 4 ml of the concentrated plasma. The platelets obtained from the used equal volume of blood, that is from 30 ml of full blood were added back to the 4 ml of concentrated plasma and alginate. The mixture was stirred and used as an occlusive agent in the dog splenic study as in example 3. Chitosan cationic (0.5 g) obtained from Protan was dissolved in 0.2% acetic acid and 4 ml of the concentrated plasma was added. The platelets obtained from the used equal volume of blood, that is from 30 ml of full blood were added back to the 4 ml of concentrated plasma and alginate. The mixture was stirred and used for occlusion in the dog's splenic vein as in Example 3.

EXAMPLE 6

Preparation of Autologous Plasma and Polymer Containing Occlusive Agent

This example illustrates preparation of occlusive hemostatic platelet-rich plasma/poly-L-lysine containing type 2 agent.

A 30 ml blood sample was drawn from a dog and placed into 0.1055M buffered sodium citrate solution. The tubes were centrifuged at 770×g for 3 minutes and a 15 ml platelet-rich plasma sample was removed. The plasma was centrifuged a second time at 2000×g. Then, the plasma was removed and the platelets were saved. The plasma was concentrated by centrifugation through a 30,000 MW cut off filter obtained from CentriCell Polysciences, Inc. for 20 minutes. The plasma was concentrated by a factor of 7–8, that is 270–390 mg of fibrinogen present in 100 ml of normal plasma was concentrated to >2000 mg/100 ml. Sodium alginate (0.2–3%) obtained from Kelco Gel LV, Merck & Co., San Diego, Calif., was dissolved in 4 ml of the concentrated plasma. The platelets obtained from the used equal volume of blood, that is from 30 ml of full blood were added back to the 4 ml of concentrated plasma and alginate. The mixture was stirred and used as an occlusive agent in the dog splenic study as in Example 3.

Chitosan cationic (0.5 g) obtained from Protan was dissolved in 0.2% of acetic acid and 4 ml of the concentrated plasma was added. The platelets obtained from the used equal volume of blood, that is from 30 ml of full blood were added back to the 4 ml of concentrated plasma and alginate. The mixture was used for occlusion of the dog's splenic vein as in Example 3. Poly-L-lysine (1 g) obtained from Sigma was dissolved in 4 ml of the concentrated plasma. The platelets obtained from the used equal volume of blood, that is from 30 ml of full blood were added back to the 4 ml concentrated plasma and alginate. The mixture was used for determination of its hemostatic occlusive properties.

The occlusive agent containing poly-L-lysine (1/ml) was injected into the splenic vein of the dog. The dog was left and observed for 3 months and was the injected with contrast medium to observe whether the occlusion was complete and permanent or whether there was recanalization through the occlusion plug. At that time, there seemed to a semi-permanent occlusion with only small recanalization through the occlusion plug.

What is claimed is:

1. An angiographic vascular occlusion agent injected in situ into a bleeding vessel or a site of injury comprising a biocompatible polymer selected from the group consisting of chitin, and chitosan in a mixture With alginate or with poly-L-amino acid, said polymer being able to gel in the presence of an endogenously present or exogenously added divalent cation.

2. The agent of claim 1 wherein the polymer is the chitosan in a mixture with alginate selected from the group consisting of sodium alginate, magnesium alginate, calcium alginate, barium alginate and strontium alginate.

3. The agent of claim 2 dissolved in an aqueous solution in the amount from about 0.001 to about 20%.

4. The agent of claim 3 wherein the divalent cation is calcium present endogenously or added to the solution of claim 3 in the amount from about 0.1 to 3%.

5. The agent of claim 1 wherein the polymer is chitosan in a mixture with the poly-L-amino acid selected from the group consisting of poly-L-lysine, poly-L-arginine, poly-L-glutamic acid, poly-L-histidine and poly-α-D-glutamic acid.

6. The agent of claim 5 dissolved in an aqueous solution in the amount from about 0.001 to about 30%.

7. The agent of claim 6 wherein the divalent cation is calcium present endogenously or added to the solution of claim 6 in amount from about 0.1 to about 3%.

8. The agent of claim 1 wherein the biopolymer is chitosan or chitin.

9. The agent of claim 8 wherein the chitosan is chitosan-polyamine or chitosan-cationic present in the amount from about 0.1 to about 10%.

10. An angiographic vascular occlusion agent injected in situ into a bleeding vessel or a site of injury, said agent comprising platelet-rich plasma wherein the plasma is concentrated from about 5 to about 10 times, and a biocompatible polymer selected from the group consisting of chitosan, chitin, and chitosan in a mixture with alginate, or with a poly-L-amino acid.

11. The agent of claim 10 wherein the biocompatible polymer is chitosan in a mixture with the alginate selected from the group consisting of sodium alginate, magnesium alginate, calcium alginate, barium alginate, strontium alginate and a mixture thereof.

12. The agent of claim 11 wherein a ratio of the polymer to the platelet-rich plasma is from about 0.01:99.99% to about 30:70%, w/w.

13. The agent of claim 12 causing a temporary, semipermanent or permanent occlusion depending on the proportionate ratio of liquid composition of the biopolymer to concentrated plasma wherein the higher ratio of polymer to concentrated plasma results in a more permanent occlusion.

14. The agent of claim 13 wherein the occlusion is semi-permanent and the concentration of the biopolymer to concentrated plasma is about 20 to 30%.

15. The agent of claim 14 wherein the plasma is concentrated from about 7 to about 8 times.

16. The agent of claim 15 wherein the platelet-rich plasma is autologous.

17. The agent of claim 16 wherein the polymer is dissolved in about 0.1 to about 3% calcium chloride solution.

18. The agent of claim 17 wherein the biopolymer is dissolved in an aqueous solution.

19. The agent of claim 10 additionally containing from about 0.1 to about 3% calcium chloride.

20. The agent of claim 10 wherein the biopolymer is chitosan.

21. The agent of claim 20 wherein the chitosan is chitosan-polyamine or chitosan-cationic.

22. The method of forming an angiographic vascular occlusion comprising administering in situ to a bleeding vessel or a site of injury an aqueous solution of a biocompatible polymer selected from the group consisting of alginate, chitosan, poly-L-amino acid and a mixture thereof, said polymer being able to gel in situ in the presence of an endogenously present or exogenously added divalent cation.

23. The method of claim 22 comprising steps:

(a) preparing an aqueous solution of a biocompatible polymer;

(b) inserting a catheter with attached needle to a site proximate to a bleeding site, lesion, ulcer or fistula;

(c) injecting the solution of the biocompatible polymer through the needle in situ;

(d) effecting the gelling of the polymer through the endogenously present or added divalent cation.

24. The method of claim 23 additionally containing step (e) injecting an aqueous solution of about 0.1 to about 3% of divalent cation simultaneously with the solution of biocompatible polymer.

25. The method of claim 24 wherein the solution of biocompatible polymer additionally contains platelet-rich plasma concentrate.

26. The method of claim 25 wherein the solution of biocompatible polymer additionally contains from about 0.1 to about 3% calcium chloride.

27. The method of claim 26 wherein the platelet-rich plasma is autologous.

28. The method of claim 27 wherein the biocompatible polymer is sodium alginate, chitosan-polyamine, chitosan-cationic or poly-L-lysine.

29. The method of claim 28 wherein the biocompatible polymer is sodium alginate dissolved in sterile water or saline solution in amount from about 1 to about 10%.

* * * * *

UNITED STATES PATENT AND TRADEMARK OFFICE
CERTIFICATE OF CORRECTION

PATENT NO. : 5,614,204
DATED : MARCH 25, 1997
INVENTOR(S) : KENT C. COCHRUM

It is certified that error appears in the above-identified patent and that said Letters Patent is hereby corrected as shown below:

Column 5, line 5, delete "plasm" and insert --plasma--.

Signed and Sealed this

Twenty-third Day of December, 1997

Attest:

Attesting Officer

BRUCE LEHMAN

Commissioner of Patents and Trademarks